United States Patent [19]

Enomoto et al.

[11] Patent Number: 4,954,626
[45] Date of Patent: Sep. 4, 1990

[54] TETRAHYDROINDAZOLYL-BENZOXAZINES, THEIR PRODUCTION AND USE

[75] Inventors: Masayuki Enomoto, Takarazuka; Eiki Nagano, Tokyo; Toru Haga, Toyonaka; Kouichi Morita, Kasai; Ryo Sato, Tokyo, all of Japan

[73] Assignee: Sumitomo Chemical Company, Limited, Osaka, Japan

[21] Appl. No.: 326,214

[22] Filed: Mar. 20, 1989

Related U.S. Application Data

[62] Division of Ser. No. 234,619, Aug. 22, 1988, Pat. No. 4,877,444.

[30] Foreign Application Priority Data

Aug. 27, 1987 [JP] Japan .................. 62-213946
Feb. 24, 1988 [JP] Japan .................. 63-42922

[51] Int. Cl.⁵ .......................... C07D 265/36
[52] U.S. Cl. .................................. 544/105
[58] Field of Search ......................... 544/105

[56] References Cited

U.S. PATENT DOCUMENTS 4,624,699 11/1986 Nagano et al. .
4,640,707  2/1987 Nagano et al. .............. 548/369
4,670,043  6/1987 Nagano et al. .............. 544/105

FOREIGN PATENT DOCUMENTS 170191    4/1986 European Pat. Off. .
208374    8/1986 European Pat. Off. .
0237899   9/1987 European Pat. Off. .
61-30586  2/1986 Japan .
61-76486  4/1986 Japan .
62-51685  9/1987 Japan .
62-277383 12/1987 Japan .

Primary Examiner—Mukund J. Shah
Assistant Examiner—E. C. Ward
Attorney, Agent, or Firm—Birch, Stewart, Kolasch & Birch

[57] ABSTRACT

A compound of the formula:

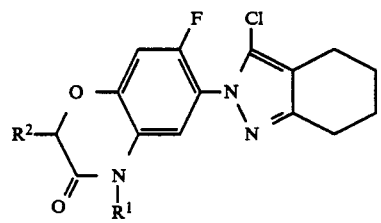

wherein $R^1$ is a $C_1$–$C_6$ alkyl group, a $C_3$–$C_7$ alkenyl group, a $C_3$–$C_7$ alkynyl group, a halo($C_1$–$C_5$)alkyl group, a halo($C_3$–$C_4$) alkenyl group, a halo($C_3$–$C_4$)alkynyl group, a $C_1$–$C_4$ alkoxy($C_1$–$C_2$)alkyl group, a $C_1$–$C_2$ alkylthio($C_1$–$C_2$)alkyl group and $R^2$ is a hydrogen atom or a methyl group, which is useful as a herbicide.

11 Claims, No Drawings

TETRAHYDROINDAZOLYL-BENZOXAZINES, THEIR PRODUCTION AND USE

This application is a divisional of copending application Ser. No. 071234,619, filed on Aug. 22, 1988 now U.S. Pat. No. 4,877,444.

The present invention relates to tetrahydroindazolyl-benzoxazines, their production, and use. More particularly, the invention relates to novel tetrahydroindazolylbenzoxazines, a process for producing them, and their use as herbicides.

U.S. Pat. No. 4,640,707 discloses certain oxazines useful as herbicides. Also, U.S. Pat. No. 4,670,043 discloses various tetrahydroindazoles useful as herbicides. However, these known herbicides are not sufficient in herbicidal potency or have poor selectivity between crop plants and weeds. Their herbicidal activity is thus not necessarily satisfactory.

It has now been found that tetrahydroindazolylbenzoxazines of the formula:

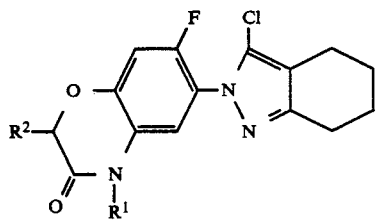

wherein $R^1$ is a $C_1$–$C_6$ alkyl group, a $C_3$–$C_7$ alkenyl group, a $C_3$–$C_7$ alkynyl group, a halo($C_1$–$C_5$) alkyl group, a halo($C_3$–$C_4$)alkenyl group, a halo($C_3$–$C_4$)alkynyl group, a $C_1$–$C_4$ alkoxy($C_1$–$C_2$)alkyl group or a $C_1$–$C_2$ alkylthio($C_1$–$C_2$)alkyl group and $R^2$ is a hydrogen atom or a methyl group show a high herbicidal potency against various weeds with a high selectivity between crop plants and weeds. Thus, they produce a strong herbicidal activity against a wide variety of weeds including broad-leaved weeds, Graminaceous weeds, Commelinaceous weeds and Cyperaceous weeds in agricultural plowed fields by foliar or soil treatment without producing any material phytotoxicity on various agricultural crops such as corn, wheat, rice plant, soybean and cotton. Examples of the broad-leaved weeds include wild buckwheat (*Polygonum convolvulus*), pale smartweed (*Polygonum lapathifolium*), common purslane (*Portulaca oleracea*), common chickweed (*Stellaria media*), common lambsquarters (*Chenopodium album*), redroot pigweed (*Amaranthus retroflexus*), radish (*Raphanus sativus*), wild mustard (*Sinapis arvensis*), shepherdspurse (*Capsella bursa-pastoris*), hemp sesbania (*Sesbania exaltata*), sicklepod (*Cassia obtusifolia*), velvetleaf (*Abutilon theophrasti*), prickly sida (*Sida spinosa*), field pansy (*Viola arvensis*), catchweed bedstraw (*Galium aparine*), ivyleaf morningglory (*Ipomoea hederacea*), tall morningglory (*Ipomoea purpurea*), field bindweed (*Convolvulus arvensis*), henbit (*Lamium amplexicaure*), jimsonweed (*Datura stramonium*), black nightshade (*Solanum nigrum*), persian speedwell (*Veronica persica*), common cocklebur (*Xanthium pensylvanicum*), common sunflower (*Helianthus annuus*), scentless chamomile (Matricaria perforata), corn marigold (*Chrysanthemum segetum*), etc. Examples of Graminaceous weeds include Japanese millet (*Echinochloa frumentacea*), barnyardgrass (*Echinochloa crusgalli*), green foxtail (*Setaria viridis*), large crabgrass (*Digitaria sanguinalis*), annual bluegrass (*Poa annua*), blackgrass (*Alopecurus myosuroides*), oats (*Avena sativa*), wild oats (*Avena fatua*), johnsongrass (*Sorghum halepense*), quackgrass (*Agropyron repens*), bermudagrass (*Cynodon dactylon*), etc. Examples of the Commelinaceous weeds include asiatic dayflower (*Commelina communis*), etc. Examples of the Cyperaceous weeds include rice flatsedge (*Cyperus iria*), etc.

The tetrahydroindazolyl-benzoxazines (I) of the invention are also effective in exterminating paddy field weeds including Graminaceous weeds such as barnyardgrass (*Echinochloa oryzicola*), broad-leaved weeds such as common falsepimpernel (*Lindernia procumbens*), indian toothcup (*Rotala indica*) and waterwort (*Elatine triandra*), Cyperaceous weeds such as water nutgrass (*Cyperus serotinus*), hardstem bulrush (*Scirpus juncoides*) and needle spikerush (*Eleocharis acicularis*), and others such as monochoria (*Monochoria vaginalis*) and arrowhead (*Sagittaria pygmaea*) without producing any phytotoxicity to rice plants on flooding treatment.

Among the tetrahydroindazolyl-benzoxazines (I), preferred are those wherein $R^1$ is a $C_3$–$C_4$ alkenyl group, a $C_3$–$C_4$ alkynyl group, a halo($C_1$–$C_5$) alkyl group or a halo($C_3$–$C_4$)alkenyl group and those wherein $R^2$ is a hydrogen atom, particularly those wherein $R^1$ is a $C_3$–$C_4$ alkynyl group or a halo($C_3$–$C_4$)alkenyl group and $R^2$ is a hydrogen atom. Typical examples of the preferred compounds are 3-chloro-2-[7-fluoro-4-propargyl-2H-1,4-benzoxazin-3(4H)-on-6yl]-4,5,6,7-tetrahydro-2H-indazole, 3-chloro-2-[7-fluoro-4-(1-butyn-3-yl)-2H-1,4-benzoxazin-3(4H)-on-6-yl]-4,5,6,7-tetrahydro-2H-indazole, 3-chloro-2-[7-fluoro-4-(2-chloro-2-propenyl)-2H-1,4-benzoxazin-3(4H)-on-6yl]-4,5,6,7tetrahydro-2H-indazole, etc.

The tetrahydroindazolyl-benzoxazines (I) of the invention can be produced by either one of the following procedures:

Procedure (A):1

The tetrahydroindazolyl-benzoxazine (I) is prepared by reacting a compound of the formula:

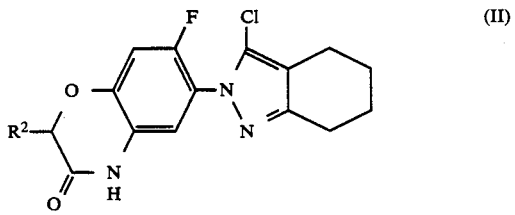

wherein $R^2$ is as defined above with a compound of the formula:

wherein $R^1$ is as defined above and X is the residue of a strong acid excluding a hydrogen atom therefrom such as a halogen atom (e.g. chlorine, bromine, iodine) or a sulfonyl group (e.g. methanesulfonyl, p-toluenesulfonyl).

The reaction is usually effected in the presence of an acid-binding agent in an inert solvent at a temperature of about 0° to 60° C. for a period of about 0.5 to 3 hours.

Normally, the compound (III) and the acid-binding agent are used respectively in amounts of about 1.0 to 1.2 equivalents and of about 1.0 to 1.2 equivalents to one equivalent of the compound (II). As the acid-binding agent, there may be used a base such as sodium hydroxide, potassium hydroxide, sodium carbonate, potassium carbonate or sodium hydride. Examples of the inert solvent are aromatic hydrocarbons (e.g. benzene, toluene, xylene), ethers (e.g. diethyl ether, diisopropyl ether, dioxane, tetrahydrofuran, diethyleneglycol dimethyl ether), acid amides (e.g. formamide, N,N-dimethylformamide, acetamide), sulfur compounds (e.g. dimethylsulfoxide, sulphorane), aqueous ammonia, etc. These may be used solely or in combination.

After completion of the reaction, the reaction mixture is subjected to an ordinary post-treatment. For instance, the reaction mixture is poured into water, and the precipitated crystals are collected by filtration. Alternatively, the reaction mixture is shaken in combination with water and a water-immiscible organic solvent for extraction, and the extract is concentrated. If desired, any conventional purification procedure such as chromatography or recrystallization may be applied to the resulting product.

According to the above process, there are obtainable the tetrahydroindazolyl-benzoxazines (I) wherein $R^1$ is an alkyl group (e.g. methyl, ethyl, propyl, isopropyl, butyl, isobutyl, sec-butyl, pentyl, hexyl), an alkenyl group (e.g. allyl, 1-methylallyl, 2-butenyl, 1-methyl-2-butenyl, 3-methyl-2-butenyl, 1,3-dimethyl-2-butenyl, 2,3-dimethyl-2-butenyl, 1,2,3-trimethyl-2-butenyl), an alkynyl group (e.g. propargyl, 1-methylpropargyl, 2-butynyl, 1-methyl-2-butynyl), an alkoxyalkyl group (e.g. methoxymethyl, ethoxymethyl, propoxymethyl, butoxymethyl, 1-methoxyethyl, 1-ethoxyethyl, 2-methoxyethyl, 2-ethoxyethyl, 2-propoxyethyl), a haloalkyl group (e.g. 2-fluoroethyl, 1,1,2,2-tetrafluoroethyl, trifluoromethyl, 2-chloroethyl), a haloalkenyl group (e.g. 2-chloroallyl, 3,3-dichloroallyl, 2,3,3-trichloroallyl), a haloalkynyl group (e.g. 3-chloropropargyl, 3bromopropargyl), an alkylthioalkyl group (e.g. methylthiomethyl), etc.

Procedure (B): 1

The tetrahydroindazolyl-benzoxazine (I) is also obtainable by reacting a hexahydroindazolyl-benzoxazine of the formula:

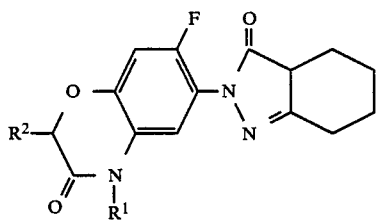

wherein $R^1$ and $R^2$ are each as defined above with a chlorinating agent.

This reaction is normally carried out in a solvent at a temperature of 80° to 200° C. for a period of 5 to 20 hours. The chlorinating agent may be employed in an excessive amount to the intermediary product (IV). Examples of the chlorinating agent are phosphorus oxychloride, thionyl chloride, phosgene, oxalic dichloride, trichloromethyl chloroformate, etc. Examples of the solvent are toluene, xylene, chloroform, etc.

The thus produced tetrahydroindazolyl-benzoxazine (I) may be subjected to an ordinary post-treatment and, when desired, purified by a per se conventional procedure such as column chromatography or recrystallization.

Typical embodiments for production of the tetrahydroindazolyl-benzoxazines (I) are illustratively shown in the following Examples.

Example 1

Preparation of 3-chloro-2-[4-ethyl-7-fluoro-2H-1,4-benzoxazin-3(4H)-on-6-yl]-4,5,6,7-tetrahydro-2H-indazole (Compound No. 1)

To a solution of 3-chloro-2-[7-fluoro-2H-1,4-benzoxazin-3(4H)-on-6-yl]-4,5,6,7-tetrahydro-2H-indazole (1.0 g) in N,N-dimethylformamide (10 ml), sodium hydride (0.3 g) and ethyl iodide (0.5 g) were successively added, and the resultant mixture was heated at 50° to 60° C., followed by stirring for 3 hours. The reaction mixture was poured into water, and the precipitated crystals were collected by filtration an purified by silica gel column chromatography using a mixture of ethyl acetate and hexane as an eluent to give Compound No. 1 (0.9 g). m.p., 101.5 ° -102.5° C.

EXAMPLE 2

Preparation of 3-chloro-2-[7-fluoro-4-propargyl-2H-1,4-benzoxazin-3(4H)-on-6-yl]-4,5,6,7-tetrahydro-2H-indazole (Compound No. 4)

A mixture of 2-(7-fluoro-4-propargyl-2H-1,4-benzoxazin-3(4H)-on-6-yl)-2,3,4,5,6,7-hexahydro-2H-indazol-3-one (1 g) and phosphorus oxychloride (0.7 g) was heated under reflux for 6 hours. After cooling, the reaction mixture was dissolved in chloroform, washed with a 5 % sodium hydroxide solution and water, dried and concentrated. The residue was purified by silica gel column chromatography to give Compound No. 4 (0.3 g). m.p., 166 ° -167° C.

In the same manner as above the compounds (I) as shown in Table 1 were obtained.

TABLE 1

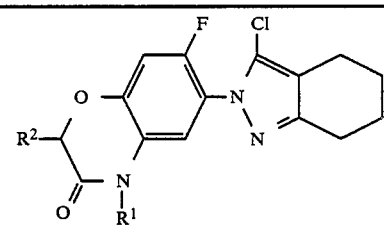

| Compound No. | $R^1$ | $R^2$ | Physical property |
|---|---|---|---|
| 1 | $C_2H_5$ | H | m.p., 101.5–102.5° C. |
| 2 | $CH_2OCH_3$ | H | m.p., 152–153° C. |
| 3 | $CH_2CH=CH_2$ | H | m.p., 131–132° C. |
| 4 | $CH_2C\equiv CH$ | H | m.p., 166–167° C. |
| 5 | $CH(CH_3)C\equiv CH$ | H | $n_D^{26.9}$ 1.5635 |
| 6 | $CH(CH_3)OCH_3$ | H | m.p., 177–178° C. |
| 7 | $CH_2OC_2H_5$ | H | m.p., 145–146° C. |
| 8 | $CH_2CH_2F$ | H | m.p., 146–147°0 C. |
| 9 | $CH(CH_3)OC_2H_5$ | H | $n_D^{27.8}$ 1.5516 |
| 10 | $CH_2CCl=CH_2$ | H | m.p., 148–149° C. |
| 11 | $CH_2C\equiv CBr$ | H | m.p., 159–160° C. |
| 12 | $CH_2SCH_3$ | H | m.p., 166–167° C. |
| 13 | $C_2H_5$ | $CH_3$ | m.p., 106–107° C. |
| 14 | $CH_2C\equiv CH$ | $CH_3$ | m.p., 154.5–155° C. |

The starting compound (II) or (IV) in the process of the invention may be produced according to the following scheme:

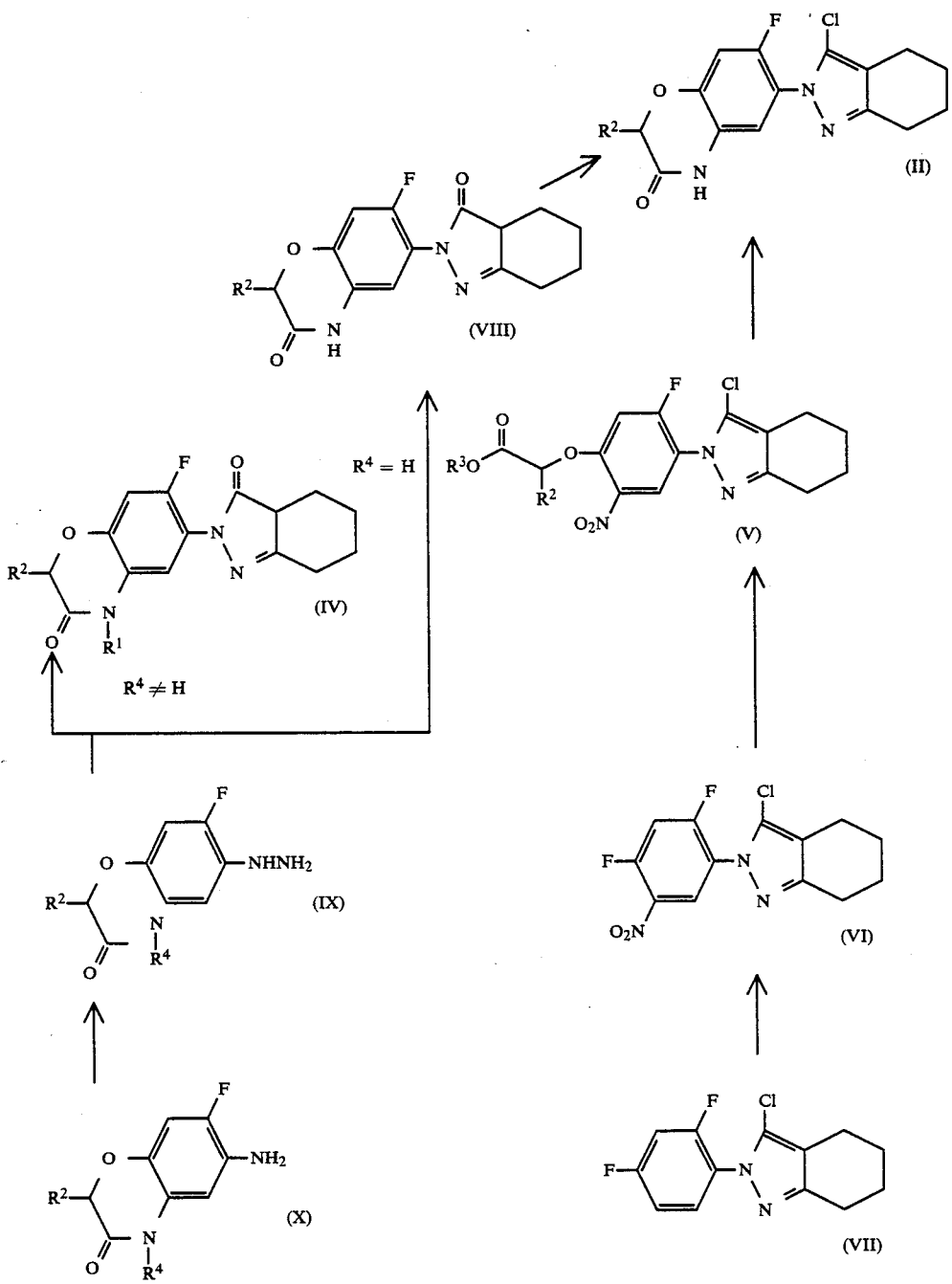

wherein $R^1$ and $R^2$ are each as defined above and $R^3$ is a $C_1$-$C_5$ alkyl group and $R^4$ is a hydrogen atom, a $C_1$-$C_6$ alkyl group, a $C_3$-$C_7$ alkenyl group, a $C_3$-$C_7$ alkynyl group, a halo($C_1$-$C_5$)alkyl group, a halo($C_3$-$C_4$)alkenyl group, a halo($C_3$-$C_4$)alkynyl group, a $C_1$-$C_4$ alkoxy($C_1$-$C_2$)alkyl group or a $C_1$-$C_2$ alkylthio($C_1$-$C_2$)alkyl group.

The reaction at each step in the above scheme will be hereinafter explained in detail.

(1) Preparation of the compound (II) from the compound (V):1

The compound (II) can be obtained by subjecting the compound (V) to reductive cyclization. The reductive cyclization may be accomplished, for instance, by treatment of the compound (V) with a reducing agent such as iron powders or by catalytic reduction of the compound (V).

Treatment with iron powders may be carried out using iron powders in an amount of about 2.5 to 10 equivalents to one equivalent of the compound (V) in the presence of a small amount of an acid (e.g. acetic acid, chloric acid) in an inert solvent at a temperature of about 50° to 200° C. for a period of about 0.5 to 10 hours. Examples of the solvent are toluene, 1,2-dichloroethane, methyl isobutyl ketone, acetic acid, water, etc. Their mixtures are also usable.

Catalytic reduction may be performed in the presence of a catalytic amount of palladium-carbon in an inert solvent (e.g. methanol, ethanol) at room temperature for a period of about 0.5 to 20 hours.

After completion of the reaction, the reaction mixture may be subjected to an ordinary post-treatment. For instance, the reaction mixture is filtered; the filtrate is combined with water, and the resultant mixture is extracted with an organic solvent, followed by concentration. When desired, any conventional purification procedure such as recrystallization or column chromatography may be applied to the resulting product.

A typical example for production of the compound (II) is illustratively shown in the following Example.

EXAMPLE 3

A suspension of 3-chloro-2-(2-fluoro-4-butyloxycarbonylmethoxy-5-nitrophenyl)-4,5,6,7-tetrahydro-2H-indazole (10 g) and iron powders (10 g) in acetic acid was refluxed for 5 hours. After completion of the reaction, the reaction mixture was filtered by the use of celite, and the filtrate was combined with water and extracted with ethyl acetate. The organic layer was concentrated, and the residue was purified by column chromatography using a mixture of hexane and ethyl acetate as an eluent to give 3chloro-2-[7-fluoro-2H-1,4-benzoxazin-3(4H)-on-6yl]-4,5,6,7-tetrahydro-2H-indazole (6.2 g). $n_D^{29.0}$ 1.5628.

$^1$H-NMR ($\delta$, CDCl$_3$): 1.5–2.0 (br, 4H), 4.6 (s, 2H), 6.77 (d, 1H, J=11 Hz), 6.92 (d, 1H, J=8 Hz), 9.8–10.1 (br, 1H).

In the same manner as above, there was obtained 3-chloro-2-[7-fluoro-2-methyl-2H-1,4-benzoxazin-3(4H)-on-6-yl]-4,5,6,7-tetrahydro-2H-indazole. m.p., 189° C.

$^1$H-NMR ($\delta$, CDCl$_3$): 1.55 (d, 3H, J=7 Hz), 1.4–2.1 (br, 4H), 2.2–2.8 (br, 4H), 4,62 q, 1H, J=7 Hz), 6.77 (d, 1H, J=10 Hz), 6.92 (d, 1H, J=8 Hz), 9.9–10.2 (br, 1H).

(2) Preparation of the compound (V) from the compound (VI): 1

The compound (V) may be produced by reacting the compound (VI) with an alpha-hydroxy acid alkyl ester of the formula:

(XI)

wherein R$^2$ and R$^3$ are each as defined above, usually in the presence of a base in an inert solvent at a temperature of about 25 ° to 200° C. for a period of about 0.5 to 10 hours. In this reaction, the compound (XI) and the base may be respectively used in amounts of about 1.0 to 1.2 equivalents and of about 1.0 to 4.0 equivalents to the compound (VI). As the base, there may be used an inorganic base such as potassium fluoride, potassium carbonate or sodium hydride. Examples of the solvent are aromatic hydrocarbons (e.g. toluene, xylene), halogenated hydrocarbons (e.g. dichloromethane, 1,2-dichloroethane), ethers (e.g. tetrahydrofuran, dioxane), etc.

After completion of the reaction, the reaction mixture is subjected to an ordinary post-treatment. For instance, the reaction mixture is poured into water, extracted with an organic solvent and concentrated. If desired, any conventional purification procedure such as chromatography or recrystallization may be adopted.

A typical embodiment for production of the compound (V) is illustratively shown in the following Example.

EXAMPLE 4

A suspension of 3-chloro-2-(2,4-difluoro-5-nitrophenyl)-4,5,6,7-tetrahydro-2H-indazole (10 g), butyl glycollate (5 g) and potassium fluoride (10 g) in dioxane (30 g) was refluxed for 1 hour. After completion of the reaction, the reaction mixture was poured into water and extracted with ethyl acetate. The extract was dried over magnesium sulfate and concentrated. The residue was purified by liquid column chromatography using a mixture of hexane and ethyl acetate as an eluent to give 3-chloro-2-(2-fluoro-4-butyloxycarbonylmethoxy-5-nitro-phenyl)-4,5,6,7-tetrahydro-2H-indazole (10.2 g). m.p., 138° –139° C.

$^1$H-NMR ($\delta$, CDCl$_3$): 0.92 (t, 3H, J=6 Hz), 1.1–2.1 (br, 8H), 2.1–2.9 (br, 4.2 (t, 2H, J=6 Hz), 4.8 (s, 2H), 6.82 (d, 1H, J=11 Hz), 8.03 (d, 1H, J=8 Hz).

In the same manner as above, there was obtained 3-chloro-2-[2-fluoro-4-(1-ethoxycarbonylethoxy-5-nitrophenyl]-4,5,6,7-tetrahydro-2H-indazole. $n_D^{28.6}$ 1.5671.

(3) Preparation of the compound (VI) from the compound (VII):

The compound (VI) is obtainable by nitrating the compound (VII) with nitric acid in conc. sulfuric acid normally at a temperature of about 0° to 30° C. for a period of about 0.3 to 3 hours. In the nitration, nitric acid is used in an amount of about 1.0 to 1.5 equivalents to the compound (VII). Post-treatment of the reaction mixture after completion of the nitration may be carried out in a per se conventional manner.

A typical embodiment for production of the compound (VI) is illustratively shown in the following Example.

EXAMPLE 5

A solution of 3-chloro-2-(2,4-difluorophenyl)4,5,6,7-tetrahydro-2H-indazole (217 g) in conc. sulfuric acid (1 kg) was cooled to 5° C., and 99 % nitric acid (67 g) was dropwise added thereto at a temperature below about 10° C., followed by stirring for 3 hours. After completion of the reaction, the reaction mixture was added to ice-water (10 kg), and the precipitated crystals were collected by filtration, washed and dried to give 3-chloro-2-(2,4-difluoro-5-nitrophenyl)-4,5,6,7-tetrahydro-2H-indazole (227 g). m.p., 117° –118 ° C. (decomp.).

$^1$H-NMR ($\delta$, CDCl$_3$): 1.7–2.1 (br, 4H), 2.3–2.9 (br, 4H), 7.2 (t, 1H, J=10 Hz), 8.28 (t, 1H, J=8 Hz).

The compound (VII) is obtainable according to the process as disclosed in U.S. Pat. No. 4,059,434.

(4) Preparation of the compound (II) from the compound (VIII): The compound (II) is obtainable from the compound (VIII) in the same manner as in Procedure (B).

Preparation of the compound (IV) or the compound (VIII) from the compound (IX):

The compound (IV) or the compound (VIII) may be produced by reacting the compound (IX) with a 2-alkoxycarbonylcyclohexanone of the formula:

(XII)

wherein R$^5$ is a C$_1$–C$_4$ alkyl group.

This reaction may be carried out in a solvent at a temperature of 80° to 200° C. for period of 0.5 to 20 hours. The compound (XII) is usually employed in an amount of 1.0 to 1.2 equivalents to the compound (IX). Examples of the solvents are toluene, xylene, acetic acid, etc.

A typical embodiment for preparation of the compound (IV) is illustratively shown in the following example.

EXAMPLE 6

A mixture of 7-fluoro-4-propargyl-2H-1,4-benzoxazin-3(4H)-on-6-ylhydrazine (1.8 g) and 2-ethoxycarbonylcyclohexanone (1.0 g) were dissolved in acetic acid (5 ml). The resultant mixture was heated under reflux for 8 hours. After cooling, the reaction mixture was concentrated under reduced pressure, and the residue was purified by silica gel column chromatography to give 0.9 g of 2-(7-fluoro-4-propargyl-2H-1,4-benzoxazin-3(4H)-on-6-yl)-2,3,4,5,6,7-hexahydro-2H-indazol-3-one. m.p., 189°–191° C.

Examples of the compound (IV) or the compound (VIII) produced in the same manner as above are shown in Table 2.

TABLE 2

(IV) or (VIII)

| R² | R⁴ | Physical property |
|---|---|---|
| H | H | m.p., 218-220° C. |
| H | C₂H₅ | m.p., 196-198° C. |
| H | CH₂C≡CH | m.p., 189-191° C. |
| CH₃ | CH₂C≡CH | m.p., 211-212° C. |

(6) Preparation of the compound (IX) from the compound (X):

The hydrazine (IX) is prepared from the aniline (X) according to the method as described in J.Chem.Soc., (c), 1970, 2106. Namely, the aniline (X) is diazotiated by reacting with an alkali metal nitrite in an amount of 1.0 to 1.2 equivalents to the former in hydrochloric acid or sulfuric acid at a temperature of about −5 ° to 5° C. for a period of about 0.5 to 24 hours. The resultant diazonium solution is then reacted with anhydrous stannous chloride in an amount of about 2 to 3 equivalents to the aniline (X) at a temperature of about −20° to 50° C. for a period of about 0.5 to 3 hours. The reaction mixture is neutralized at a temperature lower than about 10° C. and extracted with an organic solvent. The extract is dried and concentrated to give the hydrazine (IX). When desired, the product may be purified by recrystallization or column chromatography.

A typical example for production of the hydrazine (IX) is illustratively shown in the following Example.

EXAMPLE 7

A suspension of 6-amino-7-fluoro-4-propargyl-2H1,4-benzoxazin-3(4H)-one (13.0 g) in conc. hydrochloric acid (70 g) was cooled to 0° to 5° C., and a saturated solution of sodium nitrite (5.1 g) was dropwise added thereto at 0° to 5° C., followed by stirring for 2 hours. The resultant mixture was cooled to −30° C., and a solution of anhydrous stannous chloride (28.1 g) in conc. hydrochloric acid (30 g) was added thereto at once, followed by stirring at 0° to 5° C. for 3 hours. Celite (50 g) was added to the reaction mixture, which was neutralized with 10 % aqueous sodium hydroxide solution below 10° C. The resulting mixture was filtered, and the filtrate was extracted with ethyl acetate. The extract was washed with water, dried and concentrated to give 7-fluoro-4-propargyl-2H-1,4-benzoxazin-3(4H)-on-6-ylhydrazine (8.2 g).

In the same manner as above, the compounds as shown in Table 3 were obtained.

TABLE 3

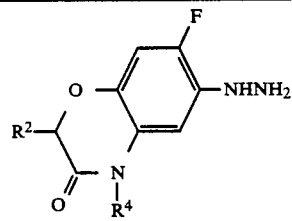

(IX)

| R² | R⁴ | Physical property |
|---|---|---|
| H | CH₂C≡CH | m.p., 82-84° C. (decomp.) ¹H-NMR (δ, CDCl₃ + d₆-DMSO): 3.1-3.2(t, 1H, J=3Hz), 3.7-4.2(br, 2H), 4.5(s, 2H), 4.6(d, 2H, J=3Hz), 6.2-6.7(br, 1H), 6.75(d, 1H, J=12Hz), 7.05(d, 1H, J=8Hz) |
| H | H | m.p., 92-94° C. (decomp.) ¹H-NMR (δ, d₆-DMSO): 3.2-4.0(br, 3H), 4.38(s, 2H), 6.55(d, 1H, J=12Hz), 6.77(d, 1H, J=8Hz), 10-11(br, 1H) |
| H | C₂H₅ | m.p., 79-82° C. (decomp.) |
| H | CH₂CH=CH₂ | m.p., 69-71° C. (decomp.) |
| CH₃ | CH₂C≡CH | m.p., 73-74° C. (decomp.) |

The aniline (X) can be produced by the method as disclosed in U.S. Pat. No. 4,640,707.

For the practical use of the tetrahydroindazolylbenzoxazine (I), it is usually formulated with conventional solid or liquid carriers or diluents as well as surface active agents or auxiliary agents into conventional preparation forms such as emulsifiable concentrates, wettable powders, suspensions and granules. The content of the tetrahydroindazolyl-benzoxazine (I) as the active ingredient in such preparation forms is normally within a range of about 0.005 to 80 % by weight, preferably of about 0.01 to 70 % by weight. Examples of the solid carrier or diluent are fine powders or granules of kaolin clay, attapulgite clay, bentonite, terra alba, pyrophyllite, talc, diatomaceous earth, calcite, walnut powders, urea, ammonium sulfate and synthetic hydrous silicate, etc. As the liquid carrier or diluent, there may be exemplified aromatic hydrocarbons (e.g. xylene, methylnaphthalene), alcohols (e.g. isopropanol, ethylene glycol, cellosolve), ketones (e.g. acetone, cyclohexanone, isophorone), soybean oil, cotton seed oil, dimethylsulfoxide, N,N-dimethylformamide, acetonitrile, water, etc.

The surface active agent used for emulsification, dispersion or spreading may be of any type, for instance, either anionic or non-ionic. Examples of the surface active agent include alkylsulfates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene polyoxypropylene block copolymer, sorbitan fatty acid esters, polyoxyethylene sorbitan fatty acid esters, etc. Examples of the auxiliary agents include ligninsulfonates, sodium alginate, polyvinyl alcohol, gum arabic, CMC (carboxymethyl cellulose), PAP (isopropyl acid phosphate), etc.

Practical embodiments of the herbicidal composition according to the present invention ar illustratively shown in the following examples wherein parts are by weight. The compound number of the active ingredient corresponds to the one in Table 1.

FORMULATION EXAMPLE 1

Fifty parts of Compound No. 1, 3 or 4, 3 parts of calcium ligninsulfonate, 2 parts of sodium laurylsulfate and 45 parts of synthetic hydrous silicate are mixed well while being powdered to obtain a wettable powder.

FORMULATION EXAMPLE 2

Five parts of any one of Compound Nos. 1 to 14, 14 parts of polyoxyethylenestyrylphenyl ether, 6 parts of calcium dodecylbenzenesulfonate, 40 parts of xylene and 35 parts of cyclohexanone are mixed well to obtain an emulsifiable concentrate.

FORMULATION EXAMPLE 3

Two parts of Compound No. 3 or 4, 1 part of synthetic hydrous silicate, 2 parts of calcium ligninsulfonate, 30 parts of bentonite and 65 parts of kaolin clay are mixed well while being powdered. The mixture is then kneaded with water, granulated and dried to obtain granules.

FORMULATION EXAMPLE 4

Twenty-five parts of Compound No. 4 or 5 are mixed with 3 parts of polyoxyethylene sorbitan monooleate, 3 parts of carboxymethyl cellulose and 69 parts of water and pulverized until the particle size of the mixture becomes less than 5 microns to obtain a suspension.

FORMULATION EXAMPLE 5

0.03 Part of Compound No. 4, 1 part of synthetic hydrous silicate, 2 parts of calcium ligninsulfonate, 30 parts of bentonite and 66.97 parts of kaolin clay are mixed well while being powdered. The mixture is then kneaded with water, granulated and dried to obtain granules.

The tetrahydroindazolyl-benzoxazine (I) thus formulated in any suitable preparation form is useful for pre-emergence or post-emergence control of undesired weeds by soil or foliar treatment as well as flood fallowing treatment. These treatments include application to the soil surface prior to or after transplanting, incorporation into the soil, etc. The foliar treatment may be effected by spraying the herbicidal composition containing the tetrahydroindazolyl-benzoxazine (I) over the top of plants. It may also be applied directly to the weeds if care is taken to keep the chemical off the crop foliage.

The tetrahydroindazolyl-benzoxazine (I) may be used together with any other herbicide to improve its activity as a herbicide, and in some cases, a synergistic effect can be expected. Further, it may be applied in combination with an insecticide, an acaricide, a nematocide, a fungicide, a plant growth regulator, a fertilizer, a soil improver, etc. Furthermore, it may be used as a herbicide applicable to agricultural plowed fields as well as paddy fields. It is also useful as a herbicide to be employed for orchards, pasture lands, lawns, forests, non-agricultural fields, etc.

The dosage of the tetrahydroindazolyl-benzoxazine (I) may vary depending on the prevailing weather conditions, the formulation used, the prevailing season, the mode of application, the soil involved, the crop and weed species, etc. Generally, however, the dosage is from about 0.01 to 80 grams, preferably from about 0.02 to 40 grams, of the active ingredient per are. The herbicidal composition of the invention formulated in the form of an emulsifiable concentrate, a wettable powder or a suspension may ordinarily be employed by diluting it with water at a volume of about 1 to 10 liters per are, if necessary, with addition of an auxiliary agent such as a spreading agent. Examples of the spreading agent include, in addition to the surface active agents as noted above, polyoxyethylene resin acid (ester), ligninsulfonate, abietylenic acid salt, dinaphthylmethanedisulfonate, paraffin, etc. The composition formulated in the form of granules may be normally applied as such without dilution.

The biological data of the tetrahydroindazolylbenzoxazines (I) as herbicides will be illustratively shown in the following Examples wherein the phytotoxicity to crop plants and the herbicidal activity on weeds were observed visually as to the degree of germination as well as the growth inhibition and rated with an index 0, 1, 2, 3, 4 or 5, the numeral "0" indicating no material difference as seen in comparison with the untreated plants and the numeral "5" indicating the complete inhibition or death of the test plants.

The compounds as shown in Table 4 were used for comparison.

TABLE 4

| Compound No. | Structure | Remarks |
|---|---|---|
| A | 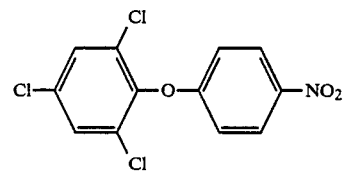 | Commercially available herbicide "chloronitrofen" |

TABLE 4-continued

| Compound No. | Structure | Remarks |
|---|---|---|
| B | [structure: 4-fluoro-phenyl with O-linked, N-ethyl amide, attached to tetrahydrophthalimide] | U.S. Pat. No. 4,640,707 |
| C | [structure: 4-fluoro-phenyl with O-linked, N-propargyl amide, attached to tetrahydrophthalimide] | U.S. Pat. No. 4,640,707 |
| D | [structure: dichloro-fluoro-phenyl with O-CH₂C≡CH, attached to chloro-tetrahydroindazole] | U.S. Pat. No. 4,670,043 |

TEST EXAMPLE 1

Cylindrical plastic pots (diameter, 10 cm; height, 10 cm) were filled with upland field soil, and the seeds of Japanese millet, oats, tall morningglory and velvetleaf were sowed therein and covered with soil. A designated amount of the test compound formulated in an emulsifiable concentrate as in Formulation Example 2 was diluted with water, and the dilution was sprayed onto the soil surface by means of a small hand sprayer at a spray volume of 10 liters per are. The test plants were grown in a greenhouse for 20 days, and the herbicidal activity was examined. The results are shown in Table 5.

TABLE 5

| Compound No. | Dosage (g/are) | Herbicidal activity | | | |
|---|---|---|---|---|---|
| | | Japanese millet | Oats | Tall morning glory | Velvet-leaf |
| 1 | 5 | 5 | 5 | 5 | 5 |
| 2 | 5 | 5 | 5 | 5 | 5 |
| 3 | 5 | 5 | 5 | 5 | 5 |
| 4 | 5 | 5 | 5 | 5 | 5 |
| 5 | 5 | 5 | 5 | 5 | 5 |
| 6 | 5 | 4 | — | 5 | 5 |
| 7 | 5 | 5 | 5 | 5 | 5 |
| 8 | 5 | 5 | 4 | 5 | 5 |
| 9 | 5 | 5 | — | 5 | 5 |
| 10 | 5 | 5 | 5 | 5 | 5 |
| 11 | 5 | 5 | 5 | 5 | 5 |
| 12 | 5 | 5 | 5 | 5 | 5 |
| 13 | 5 | 5 | 5 | 5 | 5 |
| 14 | 5 | 5 | 5 | 5 | 5 |
| A | 5 | 0 | 0 | 0 | 0 |

TEST EXAMPLE 2

Cylindrical plastic pots (diameter, 10 cm; height, 10 cm) were filled with upland field soil, and the seeds of Japanese millet, tall morningglory, radish and velvetleaf were sowed therein and cultivated in a greenhouse for 10 days. A designated amount of the test compound formulated in an emulsifiable concentrate as in Formulation Example 2 was diluted with water containing a spreading agent, and the dilution was sprayed over the foliage of the test plant by means of a small hand sprayer at a spray volume of 10 liters per are. The test plants were further grown in the greenhouse for 20 days, and the herbicidal activity was examined. The results are shown in Table 6.

TABLE 6

| Compound No. | Dosage (g/are) | Herbicidal activity | | | |
|---|---|---|---|---|---|
| | | Japanese millet | Tall morning-glory | Radish | Velvet-leaf |
| 1 | 5 | 5 | 5 | 5 | 5 |
| | 1.25 | 5 | 5 | 5 | 5 |
| 2 | 5 | 5 | 5 | 5 | 5 |
| | 1.25 | 5 | 5 | 5 | 5 |
| 3 | 5 | 5 | 5 | 5 | 5 |
| | 1.25 | 5 | 5 | 5 | 5 |
| 4 | 5 | 5 | 5 | 5 | 5 |
| | 1.25 | 5 | 5 | 5 | 5 |
| 5 | 5 | 5 | 5 | 5 | 5 |
| | 1.25 | 5 | 5 | 5 | 5 |
| 6 | 5 | 5 | 5 | 5 | 5 |
| 7 | 5 | 5 | 5 | 5 | 5 |
| | 1.25 | 5 | 5 | 5 | 5 |
| 8 | 5 | 5 | 5 | 5 | 5 |
| | 1.25 | 5 | 5 | 5 | 5 |
| 9 | 5 | 5 | 5 | 5 | 5 |
| 10 | 5 | 5 | 5 | 5 | 5 |
| 11 | 5 | 5 | 5 | 5 | 5 |
| 12 | 5 | 5 | 5 | 5 | 5 |
| 13 | 5 | 5 | 5 | 5 | 5 |
| 14 | 5 | 5 | 5 | 5 | 5 |
| A | 5 | 2 | 2 | 0 | 3 |
| | 1.25 | 0 | 0 | 0 | 0 |

TEST EXAMPLE 3

Cylindrical plastic pots (diameter, 8 cm,; height, 12 cm) were filled with paddy field soil, and the seeds of barnyardgrass (*Echinochloa oryzicola*), broad-leaved weeds (i.e. common falsepimpernel, indian toothcup, waterwort) were sowed in 1 to 2 cm depth. Water was poured therein to make a flooded condition, and rice seedlings of 3-leaf stage were transplanted therein, and the test plants were grown in a greenhouse. Six days (at that time weeds began to germinate) thereafter, a designated amount of the test compound formulated in an emulsifiable concentrate as in Formulation Example 2 and diluted with water (5 ml) was applied to the pots by perfusion. The test plants were grown for an additional 20 days in the greenhouse, and the herbicidal activity was examined. The results are shown in Table 7.

TABLE 7

Herbicidal activity

| Compound No. | Dosage (g/are) | Rice plant | Barnyard-grass | Broad-leaved weed |
| --- | --- | --- | --- | --- |
| 1 | 0.08 | — | 5 | 5 |
| 2 | 0.08 | 1 | 5 | 5 |
| 3 | 0.08 | 1 | 5 | 5 |
| 4 | 0.08 | 0 | 5 | 5 |
| 5 | 0.08 | 0 | 5 | 5 |
| 7 | 0.08 | 1 | 5 | 5 |
| 8 | 0.08 | 1 | 5 | 5 |
| 9 | 0.08 | 0 | 5 | 5 |
| A | 0.08 | 0 | 0 | 0 |
| B | 0.08 | 0 | 1 | 2 |

TEST EXAMPLE 4

Vats (33 cm×23 cm×11 cm) were filled with upland field soil, and the seeds of soybean, corn, tall morningglory, velvetleaf, Slender amaranth, black nightshade and green foxtail were sowed therein in 1 to 2 cm depth. A designated amount of the test compound formulated in an emulsifiable concentrate as in Formulation Example 2 was diluted with water, and the dilution was sprayed onto the soil surface by means of a small hand sprayer at a spray volume of 10 liters per are. The test plants were grown in a greenhouse for 20 days, and the herbicidal activity was examined. The results are shown in Table 8.

TABLE 8

| Compound No. | Dosage (g/are) | Phytotoxicity | | Herbicidal activity | | | | |
| --- | --- | --- | --- | --- | --- | --- | --- | --- |
| | | Rice plant | Corn | Tall morning-glory | Velvet-leaf | Slender amaranth | Black night-shade | Green foxtail |
| 1 | 5 | 1 | 1 | 5 | 5 | 5 | 5 | 5 |
| 2 | 5 | 0 | 1 | 5 | 5 | 5 | 5 | 4 |
| 3 | 5 | 0 | 0 | 5 | 5 | 5 | 5 | 5 |
| 4 | 2.5 | 1 | 1 | 5 | 5 | 5 | 5 | 5 |
| 5 | 5 | 0 | 1 | 5 | 5 | 5 | 5 | 5 |
| A | 5 | 0 | 0 | 0 | 1 | 1 | 1 | 0 |
| D | 2.5 | 1 | 5 | 5 | 5 | 5 | 5 | 5 |

TEST EXAMPLE

Vats (33 cm×23 cm×11 cm) were filled with upland field soil, and the seeds of corn, common cocklebur, velvetleaf, tall morningglory and black nightshade were sowed therein and cultivated for 18 days in a greenhouse. A designated amount of the test compound formulated in an emulsifiable concentrate as in Formulation Example 2 was diluted with water containing a spreading agent, and the dilution was sprayed over the foliage of the test plants by means of a small hand sprayer at a spray volume of 10 liters per are. The test plants were further grown in the greenhouse for 20 days, and the herbicidal activity was examined. At the time of the application, the test plants were generally at the 1 to 4 leaf stage and in 2 to 12 cm height, although the growing stage of the test plants varied depending on their species. The results are shown in Table 9.

TABLE 9

| Compound No. | Dosage (g/are) | Herbicidal activity | | | | |
| --- | --- | --- | --- | --- | --- | --- |
| | | Corn | Common cocklebur | Velvet-leaf | Tall morning-glory | Black night-shade |
| 3 | 0.32 | 1 | 4 | 5 | 5 | 5 |
| 4 | 0.32 | 1 | 5 | 5 | 5 | 5 |
| A | 0.32 | 0 | 0 | 0 | 0 | 0 |
| D | 0.32 | 3 | 5 | 5 | 5 | 5 |

TEST EXAMPLE 6

Wagner's pots (1/5000 are) were filled with paddy field soil, and the seeds of barnyardgrass (*Echinochloa oryzicola*), broad-leaved weeds (i.e. common falsepimpernel, indian toothcup, waterwort) were sowed in 1 to 2 cm depth. Water was poured therein to make a flooded condition, and rice seedlings of 3-leaf stage were transplanted therein, and the test plants were grown in a greenhouse. Four days (at that time barnyardgrass began to germinate) thereafter a designated amount of the test compound formulated in an emulsifiable concentrate as in Formulation Example 2 and diluted with water (10 ml) was applied to the pots by perfusion. The test plants were grown for an additional 20 days in the greenhouse, and the herbicidal activity was examined. The results are shown in Table 10. At the time of the treatment, the depth of water in the pots was kept at 4 cm and following two days, water was permitted to leak a volume corresponding to a 3 cm depth per day.

TABLE 10

| Compound No. | Dosage (g/are) | Herbicidal activity | | |
|---|---|---|---|---|
| | | Rice plant | Barnyard-grass | Broad-leaved weed |
| 1 | 0.04 | 1 | 5 | 5 |
| 2 | 0.04 | 1 | 5 | 5 |
| 3 | 0.04 | 1 | 5 | 5 |
| 4 | 0.04 | 1 | 5 | 5 |
| A | 0.04 | 0 | 0 | 0 |
| B | 0.04 | 0 | 0 | 1 |

TEST EXAMPLE 7

Wagner's pots (1/5000 are) were filled with paddy field soil, and the seeds of barnyardgrass (*Echinochloa oryzicola*), broad-leaved weeds (i.e. common falsepimpernel, indian toothcup, waterwort) were sowed in 1 to 2 cm depth. Water was poured therein to make a flooded condition, and rice seedlings of 2-leaf stage were transplanted therein, and the test plants were grown in a greenhouse. Five days (at that time weeds began to germinate) thereafter, a designated amount of the test compound formulated in an emulsifiable concentrate as in Formulation Example 2 and diluted with water (10 ml) was applied to the pots by perfusion. The test plants were grown for an additional 20 days in the greenhouse, and the herbicidal activity was examined. The results are shown in Table 11. At the time of the treatment, the depth of water in the pots was kept at 4 cm and following two days, water was permitted to leak a volume corresponding to a 3 cm depth per day.

TABLE 11

| Compound No. | Dosage (g/are) | Herbicidal activity | | |
|---|---|---|---|---|
| | | Rice plant | Barnyard-grass | Broad-leaved weed |
| 1 | 0.08 | 1 | 5 | 5 |
| | 0.02 | 0 | 5 | 5 |
| | 0.005 | 0 | 4 | 2 |
| 2 | 0.08 | 1 | 5 | 5 |
| | 0.02 | 0 | 5 | 5 |
| | 0.005 | 0 | 3 | 2 |
| 3 | 0.08 | 1 | 5 | 5 |
| | 0.02 | 0 | 5 | 5 |
| | 0.005 | 0 | 5 | 4 |
| 4 | 0.08 | 1 | 5 | 5 |
| | 0.02 | 0 | 5 | 5 |
| | 0.005 | 0 | 5 | 4 |
| | 0.0025 | 0 | 3 | 1 |
| 5 | 0.08 | 1 | 5 | 5 |
| | 0.02 | 0 | 5 | 4 |
| | 0.005 | 0 | 3 | 1 |
| 7 | 0.08 | 1 | 5 | 5 |
| | 0.02 | 0 | 5 | 4 |
| | 0.005 | 0 | 3 | 1 |
| 10 | 0.08 | 0 | 5 | 5 |
| | 0.02 | 0 | 5 | 5 |
| | 0.005 | 0 | 3 | 3 |
| 11 | 0.08 | 0 | 5 | 5 |
| | 0.02 | 0 | 5 | 5 |
| | 0.005 | 0 | 3 | 2 |
| 14 | 0.08 | 0 | 5 | 5 |
| | 0.02 | 0 | 5 | 5 |
| | 0.005 | 0 | 3 | 3 |
| B | 0.08 | 1 | 3 | 2 |
| | 0.02 | 0 | 0 | 0 |
| C | 0.08 | 1 | 5 | 4 |
| | 0.02 | 0 | 3 | 2 |
| | 0.005 | 0 | 0 | 0 |
| D | 0.08 | 2 | 5 | 5 |
| | 0.02 | 1 | 4 | 5 |
| | 0.005 | 0 | 3 | 3 |
| | 0.0025 | 0 | 0 | 0 |

What is claimed is:

1. A compound of the formula:

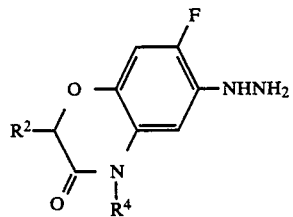

wherein $R^2$ is a hydrogen atom or a methyl group and $R^4$ is a hydrogen atom, a $C_1$-$C_6$ alkyl group, a $C_3$-$C_7$ alkenyl group, a $C_3$-$C_7$ alkynyl group, a halo($C_1$-$C_5$)alkyl group, a halo($C_3$-$C_4$)alkenyl group, a halo($C_3$-$C_4$)alkynyl group, a $C_1$-$C_4$ alkoxy($C_1$-$C_2$)alkyl group or a $C_1$-$C_2$ alkylthio($C_1$-$C_2$)alkyl group.

2. The compound according to claim 1, wherein $R^2$ is a hydrogen atom.

3. The compound according to claim 1, wherein $R^4$ is a hydrogen atom, a $C_3$-$C_4$ alkenyl group, a $C_3$-$C_4$ alkynyl group, a halo($C_1$-$C_5$)alkyl group or a halo($C_3$-$C_4$)alkenyl group.

4. The compound according to claim 1, wherein $R^4$ is a hydrogen atom, a $C_3$-$C_4$ alkynyl group or a halo($C_3$-$C_4$)alkenyl group.

5. The compound according to claim 1, wherein $R^4$ is a $C_3$-$C_4$ alkynyl group or a halo($C_3$-$C_4$)alkenyl group.

6. The compound according to claim 1, wherein $R^2$ is a hydrogen atom and $R^4$ is a $C_3$-$C_7$ alkynyl group.

7. The compound according to claim 1, wherein $R^2$ is a hydrogen atom and $R^4$ is a propargyl group.

8. The compound according to claim 1, wherein $R^2$ and $R^4$ are both hydrogen atoms.

9. The compound according to claim 1, wherein $R^2$ is a hydrogen atom and $R^4$ is an ethyl group.

10. The compound according to claim 1, wherein $R^2$ is a hydrogen atom and $R^4$ is a propenyl group.

11. The compound according to claim 1, wherein $R^2$ is a methyl group and $R^4$ is a propargyl group.

* * * * *